United States Patent [19]

Lindner et al.

[11] 4,237,330
[45] Dec. 2, 1980

[54] ISOLATION OF BUTADIENE FROM A C$_4$-HYDROCARBON MIXTURE

[75] Inventors: Alfred Lindner, Bobenheim-Roxheim; Klaus Volkamer, Frankenthal; Ulrich Wagner, Limburgerhof, all of Fed. Rep. of Germany

[73] Assignee: BASF Aktiengesellschaft, Fed. Rep. of Germany

[21] Appl. No.: 44,029

[22] Filed: May 31, 1979

[30] Foreign Application Priority Data

Jul. 28, 1978 [DE] Fed. Rep. of Germany ....... 2833195

[51] Int. Cl.$^3$ .............................................. C07C 7/00
[52] U.S. Cl. .................................. 585/807; 585/808; 585/810; 585/860; 585/865; 423/579; 203/78; 208/313
[58] Field of Search ............... 585/810, 865, 807, 808, 585/860; 423/579; 203/78; 208/313

[56] References Cited

U.S. PATENT DOCUMENTS

| 3,518,056 | 6/1970 | Klett | 203/78 |
| 4,162,198 | 7/1979 | Stockburger et al. | 585/865 |

*Primary Examiner*—Veronica O'Keefe
*Attorney, Agent, or Firm*—Keil & Witherspoon

[57] ABSTRACT

A process for isolating butadiene by means of a selective solvent from a C$_4$-hydrocarbon mixture which contains butadiene, small amounts of oxygen, hydrocarbons which are more soluble than butadiene in the selective solvent and hydrocarbons which are less soluble than butadiene in the selective solvent, wherein the C$_4$-hydrocarbon mixture is separated, by extractive distillation, into a distillate containing the less soluble hydrocarbons, a stream of butadiene and a stream containing the more soluble hydrocarbons, a mixture of oxygen and C$_4$-hydrocarbons is separated out of the C$_4$-hydrocarbon mixture in a distillation zone upstream of the extractive distillation, and the bottom product is fed to the extractive distillation.

7 Claims, 1 Drawing Figure

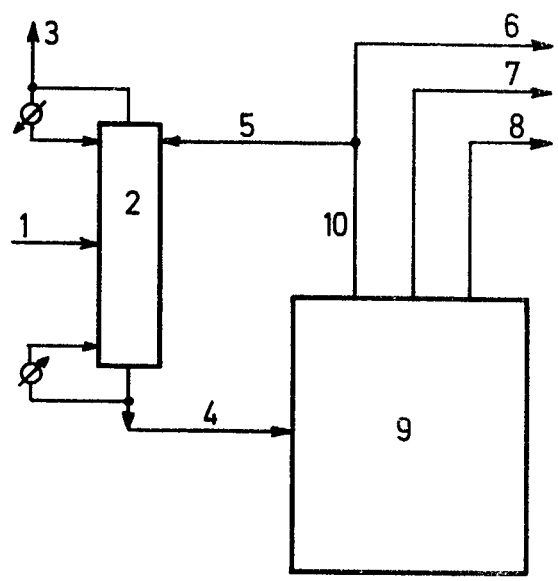

ISOLATION OF BUTADIENE FROM A C₄-HYDROCARBON MIXTURE

The present invention relates to a process for isolating butadiene from a C₄-hydrocarbon mixture containing butadiene and small amounts of oxygen.

It is known to isolate butadiene from a butadiene-containing C₄-hydrocarbon mixture by extractive distillation, using a selective solvent. The butadiene obtained from the extractive distillation is in general subsequently subjected to a conventional distillation.

The butadiene-containing C₄-hydrocarbon mixtures can in some cases contain small amounts of oxygen which can lead to undesirable polymer formation in the butadiene plant, thereby substantially reducing the time between plant shutdowns. Such C₄-hydrocarbon mixtures containing small amounts of oxygen are obtained, for example, in plants for the manufacture of butadiene-styrene copolymers, as a waste stream, containing styrene and oxygen, after the polymerization; this stream can, for example, be combusted, but is advantageously recycled to a butadiene extraction plant.

Further, C₄-hydrocarbon mixtures obtained from ethylene plants can contain small amounts of oxygen, for example if there is a fault in the ethylene plant or if the C₄-hydrocarbon mixtures are not transported under proper conditions.

It has already been proposed to remove the oxygen from the oxygen-containing C₄-hydrocarbon mixtures by evaporation, or by stripping with nitrogen. However, this method entails large losses of hydrocarbons.

It is an object of the present invention to provide a process for isolating butadiene by means of a selective solvent from a C₄-hydrocarbon mixture containing small amounts of oxygen, in which process the formation of undesirable polymers in the butadiene plant can be prevented without entailing large losses of hydrocarbons.

We have found that this and other objects are achieved, according to the invention, in a process for isolating butadiene, by means of a selective solvent, from a C₄-hydrocarbon mixture which contains butadiene, small amounts of oxygen, hydrocarbons which are more soluble than butadiene in the selective solvent and hydrocarbons which are less soluble than butadiene in the selective solvent, wherein the C₄-hydrocarbon mixture is separated, by extractive distillation, into a distillate containing the less soluble hydrocarbons, a stream of butadiene and a stream containing the more soluble hydrocarbons, a mixture of oxygen and C₄-hydrocarbons is separated out of the C₄-hydrocarbon mixture in a distillation zone upstream of the extractive distillation, and the bottom product is fed to the extractive distillation.

Using the novel process it is possible to isolate butadiene from a C₄-hydrocarbon mixture without oxygen being carried into the plant by the hydrocarbons, so that the process can be carried out continuously for long periods.

The C₄-hydrocarbon mixtures to be employed for the isolation of butadiene are obtained as a hydrocarbon fraction in, for example, the manufacture of ethylene and/or propylene by thermal cracking of a petroleum fraction, for example of liquefied petroleum gas (LPG), naphtha, gas oil and the like. Further, such C₄-fractions are obtained on catalytic dehydrogenation of n-butane and/or n-butene. Suitable C₄-hydrocarbon mixtures of relatively high butadiene content are also obtained in the manufacture of polybutadiene or butadiene-styrene copolymers. The C₄-hydrocarbon mixture as a rule contains butanes, n-butene, isobutene, butadiene, vinylacetylene, ethylacetylene and 1,2-butadiene and may contain styrene, vinylcyclohexane, small amounts of C₃-hydrocarbons and C₅-hydrocarbons. The C₄-hydrocarbon mixtures can contain small amounts of oxygen, for example as a result of faults in the stage of production of the C₄-hydrocarbon mixtures, or as a result of leaks or of insufficient nitrogen flushing of the equipment, pipe systems and transport vessels, or as a result of initiation with oxygen having been used in the manufacture of polybutadiene or butadiene-styrene copolymers. In general, the C₄-hydrocarbon mixtures to be employed according to the invention have oxygen contents of from 0.0001 to 1 percent by weight, in most cases from 0.001 to 0.5 percent by weight. However, the process according to the invention is also applicable to C₄-hydrocarbon mixtures having higher oxygen contents.

Examples of suitable selective solvents are carboxylic acid amides, e.g. dimethylformamide, diethylformamide, dimethylacetamide, formylmorpholine, acetonitrile, furfurol, N-methylpyrrolidone, butyrolactone, acetone and mixtures of these with water. The use of N-methylpyrrolidone as the selective solvent is particularly advantageous.

Examples of hydrocarbons which are more soluble than butadiene in the selective solvent are vinylacetylene, ethylacetylene and 1,2-butadiene. Examples of hydrocarbons which are less soluble than butadiene in the selective solvent are the butanes, the n-butenes and isobutene.

The extractive distillation can be carried out using one extractive distillation zone. However, the process for isolating butadiene is particularly advantageously carried out using two successive extractive distillation zones, the same selective solvent being used in both. For example, in the first stage of the extractive distillation a distillate (raffinate) containing the less soluble hydrocarbons, and an extract containing butadiene, the more soluble hydrocarbons and the selective solvent are obtained. The extract is freed from the selective solvent, giving a mixture of butadiene and the more soluble hydrocarbons. In a second extractive distillation zone, this mixture is subjected to a second extractive distillation with the selective solvent, giving butadiene as the distillate and an extract which contains the more soluble hydrocarbons, including the higher acetylenes, any residual butadiene, and the selective solvent. The extract obtained is subsequently freed from the selective solvent, giving a hydrocarbon stream which contains the more soluble hydrocarbons, including the C₄-acetylenes.

In general, the butadiene obtained from the extractive distillation is subjected to a subsequent distillation, for example in one or two distillation columns, in order to remove small amounts of propylene and C₅-hydrocarbons which may still be present.

However, the distillative removal of propyne and C₅-hydrocarbons which may have been present in the C₄-hydrocarbon starting mixtures can also be effected in one or more, for example 2, distillation columns upstream of the extractive distillation, for example in columns which are interposed between the upstream distillation zone for the removal of oxygen and the extractive distillation.

The oxygen-containing $C_4$-hydrocarbon mixtures obtained from the manufacture of styrene-butadiene copolymers as a rule still contain some styrene and may contain vinylcyclohexene. These $C_4$-hydrocarbon mixtures are also generally subjected, after the oxygen removal according to the invention, to a distillation, for example in one or more, e.g. 2, distillation columns, upstream of the extractive distillation, so as to remove styrene and any vinylcyclohexene present.

According to the invention, a mixture of oxygen and $C_4$-hydrocarbons is isolated, advantageously as the top product, from the initial $C_4$-hydrocarbon mixture, containing small amounts of oxygen, in a distillation zone upstream of the extractive distillation, the bottom product of the upstream distillation zone being fed to the extractive distillation. In general, the mixture of oxygen and $C_4$-hydrocarbons contains from 1 to 18, preferably from 5 to 16, especially from 10 to 15, mole percent of oxygen, the upper limit of the oxygen content being determined by safety considerations.

In an advantageous embodiment of the process according to the invention, a second stream of liquid or gaseous hydrocarbon is fed to the upstream distillation zone. By using this procedure, the loss of butadiene entailed in isolating the mixture of oxygen and $C_4$-hydrocarbons can be kept very low.

In general, $C_3$ and/or $C_4$-hydrocarbons are employed as liquid or gaseous hydrocarbons fed as a second stream to the distillation zone. Advantageously, hydrocarbons having a lower butadiene content than the initial $C_4$-hydrocarbon mixture, for example having less than 90% of the butadiene content of the initial $C_4$-hydrocarbon mixture, preferably essentially butadiene-free hydrocarbons, for example containing less than 5 percent by weight, advantageously less than 1 percent by weight, of butadiene, are employed. Advantageously, saturated and/or monoolefinically unsaturated $C_3$- and/or $C_4$-hydrocarbons are used. These are advantageously in the form of mixtures, for example $C_3$- or $C_4$-hydrocarbon mixtures. Examples of suitable hydrocarbons are propane, propene, the butanes, n-butene, isobutene, the 2-butenes, 1,2-butadiene and mixtures containing these hydrocarbons. Advantageously, $C_4$-hydrocarbon mixtures are employed. In a preferred embodiment of the process, the raffinate which is obtained in the extractive distillation and which contains the butanes and butenes is used.

In general, the second hydrocarbon stream to be fed to the upstream distillation zone is introduced into the said zone at or advantageously above the feed point of the initial $C_4$-hydrocarbon mixture containing small amounts of oxygen; preferably, it is fed into the upper third, advantageously into the upper quarter, in particular into the top of the upstream distillation zone. As a result of feeding in the second hydrocarbon stream above the feed point of the initial $C_4$-hydrocarbon mixture, the top product taken off is a mixture of oxygen and $C_4$-hydrocarbons having a particularly low butadiene content, for example of less than 10 percent by weight, preferably of less than 5% by weight, because of the counter-current wash which takes place; accordingly, the loss of butadiene associated with the removal of the oxygen can be kept particularly low by using this procedure. In a preferred embodiment of the process according to the invention, the second hydrocarbon stream is admixed to the liquid reflux of the upstream distillation zone, or is introduced into the said zone in place of a liquid reflux.

Advantageously, the initial $C_4$-hydrocarbon mixture is fed into the upstream distillation zone in a middle region, extending from the middle of the distillation zone to the extent of about 80%, preferably of about 60%, especially of about 50%, into both the upper and lower halves of the upstream distillation zone. The initial $C_4$-hydrocarbon mixture and the second hydrocarbon stream can be fed to the additional distillation zone as a gas or a liquid, advantageously the latter. In general, the weight ratio of hydrocarbons in the second hydrocarbon stream to hydrocarbons in the initial $C_4$-hydrocarbon mixture is from 1:1 to 1:100, preferably from 1:2 to 1:50, especially from 1:5 to 1:20. In general, conventional distillation columns, for example packed columns or tray columns, are used for the upstream distillation zone. The bottom product of the upstream distillation column is fed to the extractive distillation.

In a further embodiment of the process according to the invention, a mixture of oxygen and $C_4$-hydrocarbons is first isolated, in the distillation zone upstream of the extractive distillation, from the initial $C_4$-hydrocarbon mixture containing small amounts of oxygen, and the bottom product of the upstream distillation zone is fed to the extractive distillation. The mixture of oxygen and $C_4$-hydrocarbons isolated from the upstream distillation zone is subsequently fed to an additional distillation zone, and at the same time a second stream of liquid or gaseous hydrocarbons is fed to this additional distillation zone, and the bottom product of the said zone is recycled into the main stream. Advantageously, the bottom product is admixed to the initial $C_4$-hydrocarbon mixture. In general, the second hydrocarbon stream to be fed to the additional distillation zone is introduced at or advantageously above the feed point of the isolated mixture of oxygen and $C_4$-hydrocarbons; preferably, the second stream is fed into the upper third, advantageously into the upper quarter, in particular into the top, of the additional distillation zone. Preferably, the second hydrocarbon stream is admixed to the liquid reflux of the additional distillation zone or is introduced into the zone in place of a liquid reflux.

The isolated mixture of oxygen and $C_4$-hydrocarbons is advantageously fed to the additional distillation zone in a middle region, extending from the middle of the distillation zone to the extent of about 80%, preferably of about 60%, especially of about 50%, into both the upper and lower halves of the additional distillation zone. The isolated mixture of oxygen and $C_4$-hydrocarbons, and the second hydrocarbon stream, can be fed to the additional distillation zone as a gas or liquid, the latter being preferred. In general, the weight ratio of hydrocarbons of the second hydrocarbon stream to hydrocarbons of the isolated mixture of oxygen and $C_4$-hydrocarbons is from 1:1 to 1:100, preferably from 1:2 to 1:50, especially from 1:5 to 1:20. In general, conventional distillation columns, for example packed columns or tray columns, are used for the additional distillation zone.

It can be advantageous not only to remove the oxygen from the initial $C_4$-hydrocarbon mixture in the upstream distillation zone but also to add polymerization inhibitors, in the conventional manner, in the subsequent extractive distillation. Examples of suitable polymerization inhibitors are furfurol, benzaldehyde, aliphatic or aromatic nitro compounds, hydroquinone, sulfur, sodium nitrite, phenolic compounds, such as 4-tert.-butylcatechol, and aromatic amines, such as naphthylamine. The tendency of butadiene to polymerize can be further reduced by such addition. These inhibitors can also be used in the distillations carried out to remove oxygen.

The FIGURE presents a schematic diagram of an embodiment of the process according to the invention. A $C_4$-hydrocarbon mixture containing small amounts of oxygen (a $C_4$-fraction from an ethylene plant) is fed through line 1 into the middle third of a distillation column 2. At the top of the column 2, a part-stream of the raffinate is fed through line 5 to a downstream butadiene isolation plant 9. At the bottom of the column 2, an oxygen-free $C_4$-hydrocarbon mixture is taken off through line 4 and is fed to the butadiene plant 9, where it is separated, by extractive distillation, using a selective solvent (N-methylpyrrolidone), into a fraction (raffinate) 10 containing the butanes and butenes, the butadiene stream 7 and the stream 8 containing the $C_4$-acetylenes. The part-stream of the raffinate remaining after branching off the stream 5 is taken off through line 6.

The Examples which follow further illustrate the invention.

EXAMPLE 1

A $C_4$-hydrocarbon mixture has the following composition:

| | |
|---|---|
| $C_3$-Hydrocarbons | 0.3% by weight |
| n-Butane | 3.9% by weight |
| Isobutane | 1.3% by weight |
| n-1-Butene | 10.8% by weight |
| Isobutene | 20.9% by weight |
| trans-2-Butene | 3.8% by weight |
| cis-2-Butene | 3.2% by weight |
| Butadiene | 52.4% by weight |
| 1,2-Butadiene | 0.4% by weight |
| Butenyne | 2.0% by weight |
| Butyne | 0.1% by weight |
| Oxygen | 0.3% by weight |

1,000 g/h of this $C_4$-hydrocarbon mixture are fed into a 10-tray column at the 5th tray. At the top of the column, 100 g/h of a raffinate from a downstream butadiene isolation plant are fed in, the raffinate having the following composition:

| | |
|---|---|
| $C_3$-Hydrocarbons | 0.4% by weight |
| Butanes | 11.7% by weight |
| Butenes | 87.8% by weight |
| Butadiene | 0.1% by weight |

At the bottom of the column, 1,070 g/h of a virtually oxygen-free (<0.5 ppm by weight of $O_2$) $C_4$-hydrocarbon mixture are taken off and fed to the butadiene isolation plant, where this mixture is separated by extractive distillation, in two successive extractive distillation zones using N-methylpyrrolidone as the selective solvent and sodium nitrite as the polymerization inhibitor, into a distillate containing the butanes and butenes, very pure butadiene and a stream containing the $C_4$-acetylenes. The column top product contains 3.3 percent by weight of butadiene, corresponding to a butadiene loss of 0.2%.

EXAMPLE 2

The procedure described in Example 1 is followed, but no raffinate is fed in. The butadiene loss in the top product is 5.8%.

We claim:
1. A process for isolating butadiene by means of selective solvent from a $C_4$-hydrocarbon mixture which contains butadiene, small amounts of oxygen, hydrocarbons which are more soluble than butadiene in the selective solvent and hydrocarbons which are less soluble than butadiene in the selective solvent, which process comprises:
   a. subjecting the $C_4$-hydrocarbon mixture to distillation in a distillation zone upstream of an extractive distillation zone, said $C_4$-hydrocarbon mixture being fed into the upstream distillation zone in a middle region extending from the middle of the distillation zone to the extent of about 80% into both the upper and lower halves of the upstream distillation zone,
   b. obtaining as overhead product from the distillation zone a mixture of oxygen and $C_4$-hydrocarbons containing from 1 to 18 mole percent of oxygen,
   c. taking off as bottom product a $C_4$-hyrocarbon mixture essentially free from oxygen,
   d. subjecting the bottom product to extractive distillation using one extractive distillation zone or two successive extractive distillation zones, the same selective solvent being used in both, and
   e. separating the bottom product by extractive distillation into a distillate containing the less soluble hydrocarbons, a stream of butadiene and a stream containing the more soluble hydrocarbons.

2. The process of claim 1, wherein a second stream of liquid or gaseous hydrocarbons comprising saturated and/or monoolefinically unsaturated $C_3$- and/or $C_4$-hydrocarbons is fed simultaneously to the upstream distillation zone.

3. The process of claim 1, wherein the mixture of oxygen and hydrocarbons obtained as top product from the distillation zone is fed to an additional distillation zone in a middle region extending from the middle of the additional distillation zone to the extent of about 80% into both the upper and lower halves of the additional distillation zone, a second stream of liquid or gaseous hydrocarbons is fed simultaneously to the additional distillation zone, and the bottom product of the additional distillation zone is recycled to the main stream.

4. The process of claims 2 or 3, wherein the second stream comprises a saturated or monoolefinicially unsaturated $C_4$-hydrocarbon, or a mixture of saturated and/or monoolefinically unsaturated $C_4$-hydrocarbons.

5. The process of claims 2 or 3, wherein the second hydrocarbon stream is fed in at or above the feed point of the oxygen-containing hydrocarbon stream of the particular distillation zone.

6. The process of claims 2 or 3, wherein the feed point of the second hydrocarbon stream is in the upper third of the particular distillation zone.

7. The process of claims 1 or 2, wherein one or more distillation columns are interposed between the upstream distillation zone and the extractive distillation.

* * * * *